(12) United States Patent
Klett et al.

(10) Patent No.: US 6,763,671 B1
(45) Date of Patent: Jul. 20, 2004

(54) PERSONAL, CLOSED-CYCLE COOLING AND PROTECTIVE APPARATUS AND THERMAL BATTERY THEREFOR

(75) Inventors: James W. Klett, Knoxville, TN (US); Lynn B. Klett, Knoxville, TN (US)

(73) Assignee: UT-Battelle, LLC, Oak Ridge, TN (US)

(*) Notice: Subject to any disclaimer, the term of this patent is extended or adjusted under 35 U.S.C. 154(b) by 0 days.

(21) Appl. No.: 10/359,892

(22) Filed: Feb. 6, 2003

(51) Int. Cl.[7] .............................. F25D 23/12; F28F 7/00; A61F 7/00
(52) U.S. Cl. .................... 62/259.3; 165/46; 607/108
(58) Field of Search ................... 62/259.3, 457.9, 62/304; 165/46, 104.14; 607/108, 104, 96

(56) References Cited

U.S. PATENT DOCUMENTS

| | | | |
|---|---|---|---|
| 5,201,365 A | * 4/1993 | Siegel | ............................ 165/46 |
| 5,269,369 A | * 12/1993 | Faghri | ............................ 607/104 |
| 6,402,775 B1 | * 6/2002 | Bieberich | ............................ 607/104 |

* cited by examiner

*Primary Examiner*—Chen Wen Jiang
(74) *Attorney, Agent, or Firm*—Kirk A. Wilson (57) ABSTRACT

A closed-cycle apparatus for cooling a living body includes a heat pickup body or garment which permits evaporation of an evaporating fluid, transmission of the vapor to a condenser, and return of the condensate to the heat pickup body. A thermal battery cooling source is provided for removing heat from the condenser. The apparatus requires no external power and provides a cooling system for soldiers, race car drivers, police officers, firefighters, bomb squad technicians, and other personnel who may utilize protective clothing to work in hostile environments. An additional shield layer may simultaneously provide protection from discomfort, illness or injury due to harmful atmospheres, projectiles, edged weapons, impacts, explosions, heat, poisons, microbes, corrosive agents, or radiation, while simultaneously removing body heat from the wearer.

6 Claims, 7 Drawing Sheets

PERSONAL, CLOSED-CYCLE COOLING AND PROTECTIVE APPARATUS AND THERMAL BATTERY THEREFOR

This invention was made with Government support under Contract No. DE-AC05-00OR22725 awarded by the United States Department of Energy. The Government has certain rights in the invention.

FIELD OF THE INVETION

The present invention relates to a self-contained, portable cooling device generally used with body armor systems and other gear which may be resistant to explosion, chemical agents or biological agents while being thin, lightweight, and flexible to provide cooling and comfort to the person wearing the garment.

BACKGROUND OF THE INVENTION

Body armor and other protective clothing systems, including vests worn by law enforcement officers, often use Kevlar® or other protective fibers, which may be coated in plastic, as a protective or projectile-resistant shield. The protective coatings and layers are necessary to assure the safe performance, but make the garment hot and uncomfortable to wear. This, in turn, decreases the mobility and, thus, the efficiency of the persons who wear them and acts as a deterrent to using protective garments and as a result, increases injuries and casualties. There have been several attempts to provide a more comfortable protective garment. For example, Parrish et al (U.S. Pat. No. 5,113,666), teach a cooling device that can be incorporated into a person's apparel to permit the transfer of water vapor from the wearer's skin. Parrish et al (U.S. Pat. No. 5,111,668), a continuation-in-part of U.S. Pat. No. 5,113,666, teach a sealed garment containing a working fluid in an evaporation section of the garment, vaporization occurring by heat generated from the person wearing the garment. Parrish et al (U.S. Pat. No. 5,289,695), a divisional of U.S. Pat. No. 5,111,668, teach cooling devices such as vests, pads or patches used in garments, including space suits, sealed hazardous material suits, and/or vests. All of these embodiments comprise a desiccant layer which is utilized in the storage of the water vapor resulting from the evaporation process.

Other examples may also be found in Scaringe et al (U.S. Pat. No. 4,856,294), Szczesuil et al (U.S. Pat. No. 5,320, 164), Faghri (U.S. Pat. No. 5,269,369), Garner (U.S. Pat. No. 5,818,693), Koon et al (U.S. Pat. No. 5,898,570), Coulon et al (U.S. Pat. No. 4,852,645), Buckley (U.S. Pat. No. 5,722,482), and Benson (U.S. Pat. No. 4,572,864). All of the above are hereby incorporated by reference.

These cooling systems, however, remain heavy and uncomfortable to the wearer. Therefore, there remains a need in the art for a portable, lightweight, thin, and flexible garment which will provide more comfortable thermal conditions under the armor vest or other protective garment and would induce people to wear them as necessary, and thereby reduce the occurrence of preventable injuries and fatalities.

Many of these cooling systems require power to drive devices such as cooling fans, microheat pumps, or thermoelectric chillers and the like. Others rely on totally passive systems, which have a marginal performance and utilize extremely expensive carbon fibers that are very brittle and cannot long survive in a rugged environment. Many systems supply chilled water to a vest with flexible cooling tubes in an attempt to distribute the cooling potential uniformly across the body. However, most of these systems do not provide uniform temperature distribution and chill one part of the body more than the others, leading to discomfort. The user often turns off the system temporarily to recover, and then turns it back on. This is inefficient and may decrease the reliability of the system.

OBJECTS OF THE INVENTION

Accordingly, it is an object of the present invention to provide a new and improved flexible cooling system for primary use as a personal device for cooling personnel who may be required to wear protective garments such as projectile-resistant shields and vests, as well as garments designed to protect against chemical agents, biological agents, radioactive agents, explosions, and the like. The cooling device and protective shield or layer may be combined as layers in a cooled protective system. The subject invention would provide an ideal system for soldiers, race car drivers, hikers, police officers, firefighters, bomb squad technicians, and other personnel who may be exposed to hostile environments.

Further and other objects of the present invention will become apparent from the description contained herein.

SUMMARY OF THE INVENTION

In accordance with one aspect of the present invention, the foregoing and other objects are achieved by a thermal-battery capable, closed-cycle apparatus for cooling the living body of a wearer which comprises: a heat pickup body configured to cover at least a portion of a living body, the heat pickup body further comprising a flexible, impermeable contact foil configured to be in proximate contact with the living body, a liquid-permeable evaporator layer disposed in surface contact with the contact foil, porous liquid conduit means disposed within and throughout the liquid permeable evaporator layer for conducting a liquid therethrough and further comprising a first non-porous connection means for communicably connecting the porous liquid conduit means, a semi-rigid, gas-permeable gas conduit layer disposed in surface contact with the liquid permeable evaporator layer and further comprising a second non-porous connection means for communicably connecting the semi-rigid gas-permeable gas conduit layer, and a flexible, impermeable cover foil disposed in surface contact with the semi-rigid gas-permeable layer, the flexible impermeable contact foil, the liquid-permeable evaporator layer, the semi-rigid gas-permeable conduit layer, and the flexible, impermeable cover foil being sealed on all edges to prevent communication between each layer and atmosphere; a condenser, the condenser further comprising a chamber and being suitably configured so that the condenser may be disposed in thermal contact with a thermal battery for transferring heat from the condenser to the thermal battery, the chamber communicably connected to the first connection means and the second connection means so that the heat pickup body, first connection means, second connection means, and condenser form a continuous sealed system; and a heat pickup body evaporating fluid contained within the sealed system.

In accordance with a second aspect of the present invention, the foregoing and other objects are achieved by a thermal-battery augmented, closed-cycle apparatus for cooling a living body which comprises: a heat pickup body configured to cover at least a portion of a living body, the heat pickup body further comprising a flexible, impermeable contact foil configured to be in proximate contact with the living body, a liquid-permeable evaporator layer disposed in surface contact with the contact foil, porous liquid conduit means disposed within and throughout the liquid permeable evaporator layer for conducting a liquid therethrough and further comprising a first non-porous connection means for communicably connecting the porous liquid conduit means, a semi-rigid, gas-permeable gas conduit layer disposed in surface contact with the liquid permeable evaporator layer and further comprising a second non-porous connection means for communicably connecting the semi-rigid gas-permeable gas conduit layer, and a flexible, impermeable cover foil disposed in surface contact with the semi-rigid gas-permeable layer; the flexible, impermeable contact foil, the liquid-permeable evaporator layer, the semi-rigid gas-permeable conduit layer, and the flexible, impermeable cover foil being sealed on all edges to prevent communication between each layer and atmosphere; a condenser, the condenser further comprising a chamber and being suitably configured so that the condenser may be disposed in thermal contact with a thermal battery for transferring heat from the condenser to the thermal battery, the chamber communicably connected to the first connection means and the second connection means so that the heat pickup body, first connection means, second connection means, and condenser form a continuous, sealed system; a heat pickup body evaporating fluid contained within the sealed system; and a thermal battery, the thermal battery further comprising: an adsorption chamber, the adsorption chamber at least partially filled with an adsorptive media, an evaporation chamber, the evaporation chamber suitably configured so that the evaporation chamber may be disposed in thermal contact with the condenser, a closable throttle valve, the throttle valve being communicably connected between the absorption chamber and the evaporation chamber; the adsorption chamber, evaporation chamber, and throttle valve configured to form a sealed thermal battery system; and, a thermal battery evaporating fluid, the thermal battery evaporating fluid contained within the sealed thermal battery system.

In accordance with a third aspect of the present invention, the foregoing and other objects are achieved by a thermal-battery capable, closed-cycle body armor protective apparatus for protecting and cooling the living body of a wearer which comprises: a heat pickup body configured to cover at least a portion of a living body, the heat pickup body further comprising a flexible, impermeable contact foil configured to be in proximate contact with the living body, a liquid-permeable evaporator layer disposed in surface contact with the contact foil, porous liquid conduit means disposed within and throughout the liquid permeable evaporator layer for conducting a liquid therethrough, the heat pickup body further comprising a first non-porous connection means for communicably connecting the porous liquid conduit means, a semi-rigid, gas-permeable gas conduit layer disposed in surface contact with the liquid permeable evaporator layer and further comprising a second non-porous connection means for communicably connecting the semi-rigid gas-permeable gas conduit layer, and a flexible, impermeable cover foil disposed in surface contact with the semi-rigid gas-permeable layer, the flexible impermeable contact foil, the liquid-permeable evaporator layer, the semi-rigid gas-permeable conduit layer, and the flexible, impermeable cover foil being sealed on all edges to prevent communication between each layer and atmosphere; a condenser, the condenser further comprising a chamber and being suitably configured so that the condenser may be disposed in thermal contact with a thermal battery for transferring heat from the condenser to the thermal battery, the chamber communicably connected to the first connection means and the second connection means so that the heat pickup body, first connection means, second connection means, and condenser form a continuous sealed system; a heat pickup body evaporating fluid contained within the sealed system; and a protective shield disposed proximate to and covering at least a portion of the heat pick-up body for protecting the living body of the wearer from illness or injury due to a hazard such as projectiles, edged weapons, impacts and explosions, as well as heat, poisons, microbes, corrosive agents, or radiation.

In accordance with a fourth aspect of the present invention, the foregoing and other objects are achieved by a thermal-battery augmented, closed-cycle body armor protective apparatus for protecting and cooling the living body of a wearer which comprises: a heat pickup body configured to cover at least a portion of a living body, the heat pickup body further comprising a flexible, impermeable contact foil configured to be in proximate contact with the living body, a liquid-permeable evaporator layer disposed in surface contact with the contact foil, porous liquid conduit means disposed within and throughout the liquid permeable evaporator layer for conducting a liquid therethrough, the heat pickup body further comprising a first non-porous connection means for communicably connecting the porous liquid conduit means, a semi-rigid, gas-permeable gas conduit layer disposed in surface contact with the liquid permeable evaporator layer and further comprising a second non-porous connection means for communicably connecting the semi-rigid gas-permeable gas conduit layer, and a flexible, impermeable cover foil disposed in surface contact with the semi-rigid gas-permeable layer, the flexible impermeable contact foil, the liquid-permeable evaporator layer, the semi-rigid gas-permeable conduit layer, and the flexible, impermeable cover foil being sealed on all edges to prevent communication between each layer and atmosphere; a condenser, the condenser further comprising a chamber and being suitably configured so that the condenser may be disposed in thermal contact with a thermal battery for transferring heat from the condenser to the thermal battery, the chamber communicably connected to the first connection means and the second connection means so that the heat pickup body, first connection means, second connection means, and condenser form a continuous sealed system; a heat pickup body evaporating fluid contained within the sealed system; and a thermal battery, the thermal battery further comprising: an adsorption chamber, the adsorption chamber at least partially filled with an adsorptive media, an evaporation chamber, the evaporation chamber suitably configured so that the evaporation chamber may be disposed in thermal contact with the condenser, a closable throttle valve, the throttle valve being communicably connected between the absorption chamber and the evaporation chamber; the adsorption chamber, evaporation chamber, and throttle valve configured to form a sealed thermal battery system; and, a thermal battery evaporating fluid, the thermal battery evaporating fluid contained within the sealed thermal battery system; and a protective shield disposed proximate to and covering at least a portion of the heat pick-up body for protecting the living body of the wearer from illness or injury due to a hazard such as projectiles, edged weapons, impacts and explosions, as well as heat, poisons, microbes, corrosive agents, or radiation.

For a better understanding of the present invention, together with other and further objects, advantages and capabilities thereof, reference is made to the following disclosure and appended claims in connection with the above-described drawings.

DETAILED DESCRIPTION OF THE INVENTION

The present invention describes a novel combination, modification or adaptation of several aspects of evaporative cooling. The invention provides a flexible evaporator, fashioned into the shape of a garment which covers the portion of the living body which is to be cooled, and which is used to take heat from the body and apply it to an evaporating fluid, many of which are well-known to the skilled artisan, to facilitate heat transfer. Suitable fluids may include but not be limited to: water, alcohols, acetone, flurocarbons (FC87, FC72, etc.), and other hydrocarbons such as ethylene chloride. This fluid, when operated under reduced pressure, evaporates and takes the heat from the living body isothermally and delivers it to the condenser. As the heat in the condenser is removed by an external cold source, the vapor is condensed and returned to the evaporator for recycling. The fluid is forced to return to the evaporator through supply tubes due to the vapor pressure generated when the fluid at the evaporator vaporizes. This type of system is typically referred to as a loop heat pipe or thernosyphon. The main advantage of this system is that it removes heat from a flexible evaporator at the appropriate boiling point, which is controlled by the internal pressure of system and the vapor pressure of the fluid, isothermally throughout the entire system. Another advantage of the system is that the condenser operates at virtually the same temperature as the evaporator, therefore eliminating problems from the high temperatures typically found at the compressor side of a heat pump. The only requirement is that an external cooling supply be used to remove the heat, i.e. thermal battery, air, water, etc. However this also can be passive and regenerable.

The temperature of the cooling side of the system or evaporator is regulated solely by the amount of heat rejected by the condenser. That is, the temperature of the cooling vest or heat pickup body can be regulated quite simply by regulating the efficiency of the condenser of the system. This can be done in the case of the thermal battery by adjusting the throttle valve in the battery. Hence, a very simple thermostat regulator is inherent in the system.

Figure 1A:
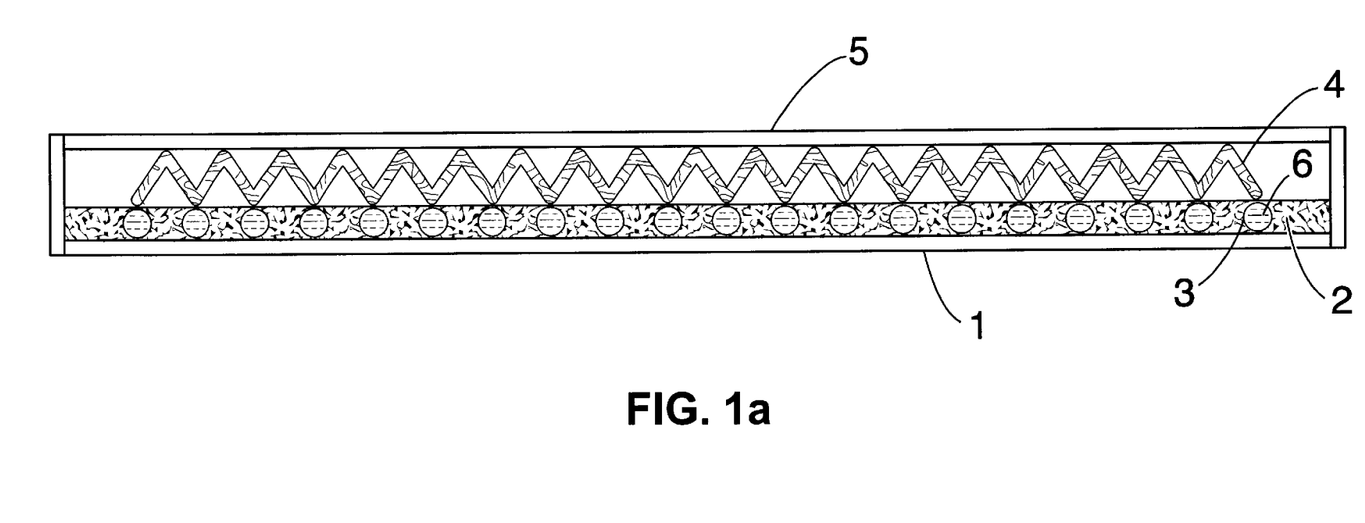
FIG. 1a is a transverse cross-sectional view of the heat pickup body.
Figure 1B:
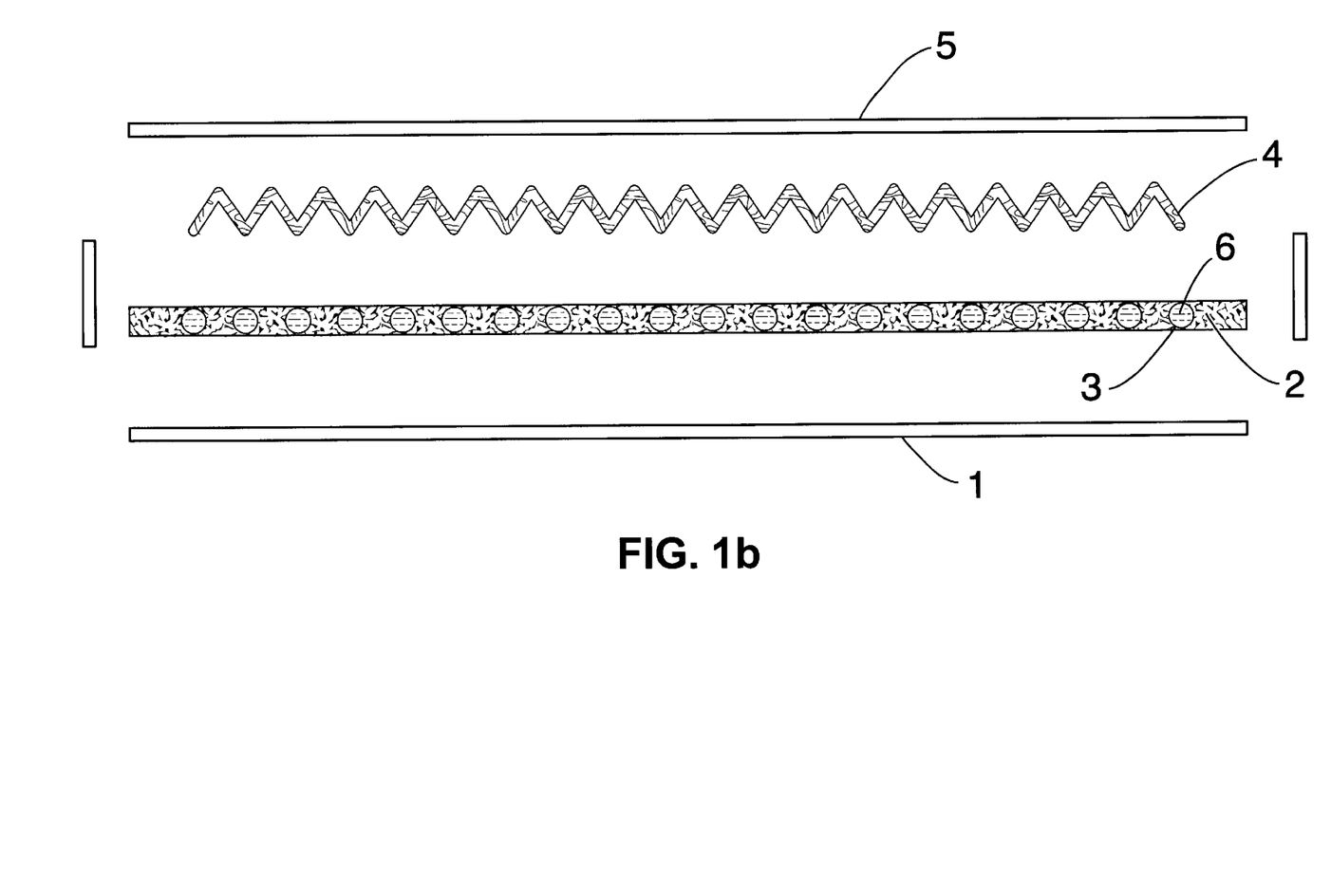
FIG. 1b is an exploded view of a transverse cross-sectional view of the heat pickup body.
Figure 2A:
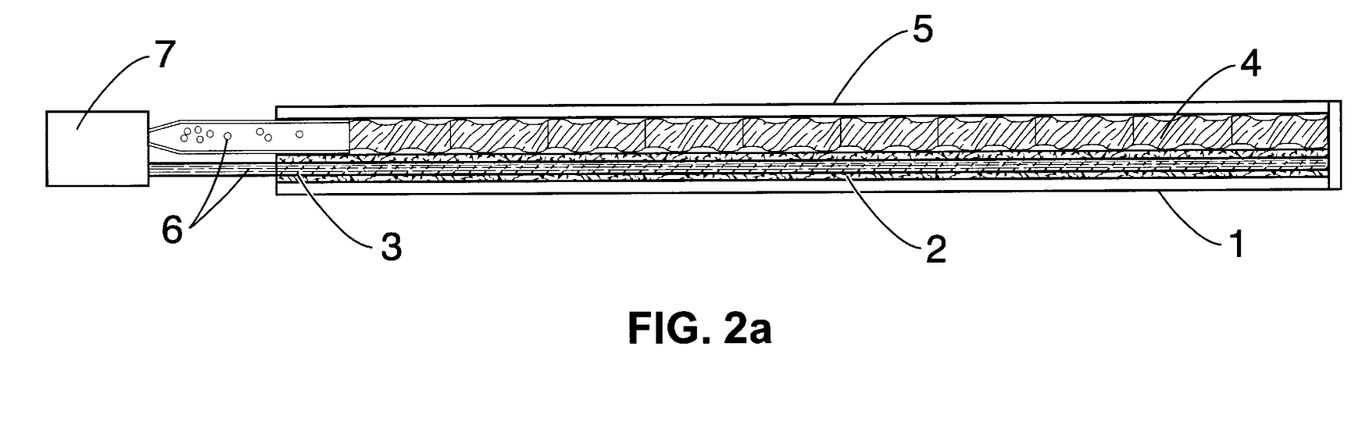
FIG. 2a is a longitudinal cross-sectional view of the heat pickup body.
Figure 2B:
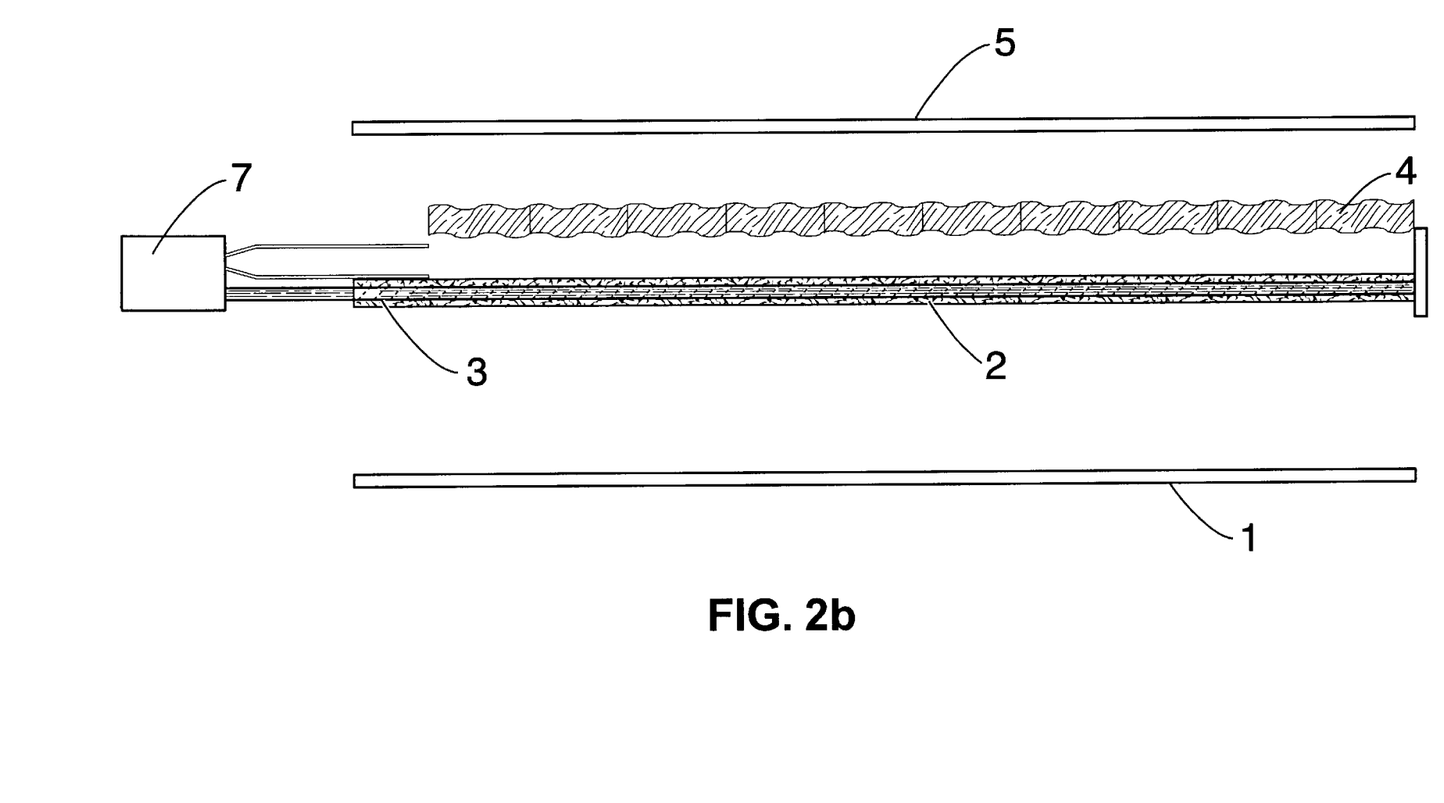
FIG. 2b is an exploded view of a longitudinal cross-sectional view of the heat pickup body.

To construct such a system, first a suitable flexible contact foil 1 is chosen for the application. This foil 1 comprises the part of the systems that gets cold and transfers heat from the heat source (living body or undergarment) in proximate or direct contact and should be durable, yet flexible enough for comfort. Onto the contact foil a porous evaporator 2 is placed, preferably joined with adhesive. The porous evaporator 2 is preferably a conductive carbon felt or woven mat, preferably made from mesophase pitch-based carbon fibers. Within this porous mat 2, many perforated tubes 3 are aligned parallel to each other, and traversing the length of the porous mat. These tubes 3 are the return lines of the system and provide a means of supplying the heat pickup body vaporating fluid 6 to the porous mat 2 for subsequent evaporation. Next, on top of the porous mat 2 is a highly permeable, yet flexible structure 4. This structure 4 should be sufficiently stiff to prevent collapse of the system during its operation under reduced pressure, but needs to be flexible enough to provide comfort to the wearer. In one embodiment the flexible structure 4 is corrugated. In another embodiment the flexible structure 4 is a spacer fabric made from polymer fibers. Last is the cover foil 5, which is preferably bonded to the flexible support structure. The entire assembly is bonded together as shown in FIGS. 1a and 2a to form a pressure-tight assembly.

Figure 3:
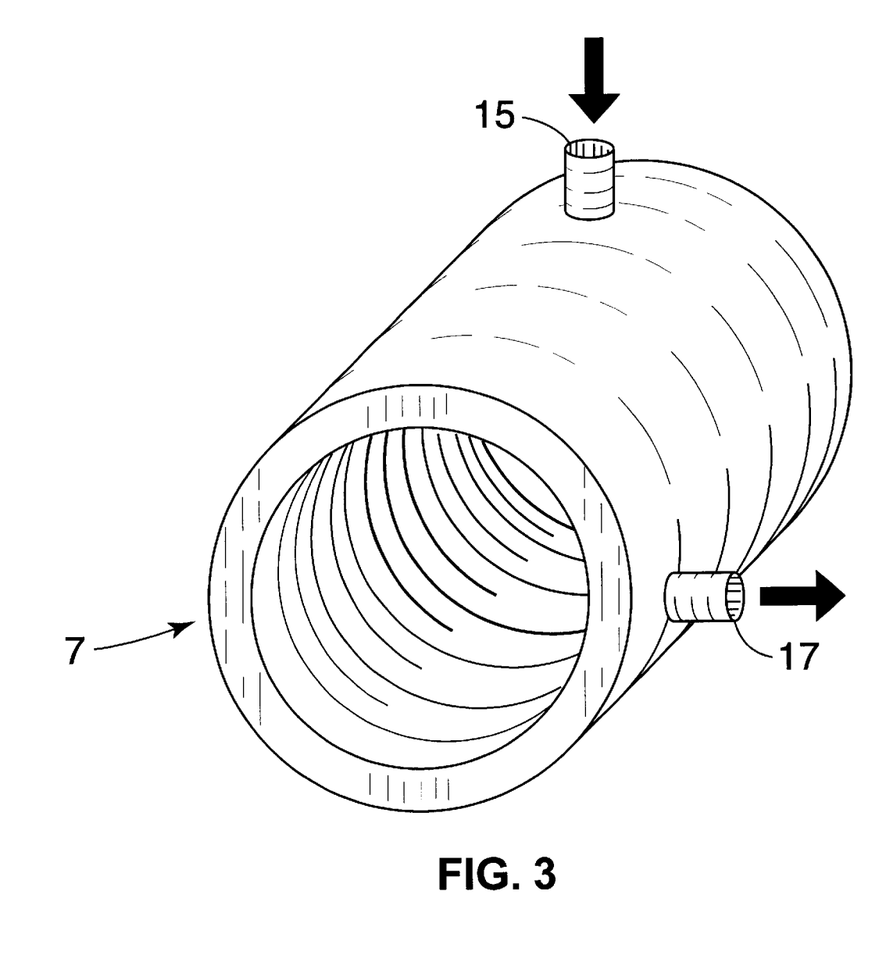
FIG. 3 shows one embodiment of a condenser.

As the heat from the body contacts the contact foil 1, it is conducted through the foil 1 to the evaporator 2 (i.e. fibrous mat), where the heat causes evaporation of the fluid 6. Note that the system may be operated under less than atmospheric pressure. The vapor is forced from the evaporator 2 into the space surrounding the support structure 4, then traverses down the system through the first nonporous connection means, which may be a line to the inlet 15 of the condenser 7. This condenser 7 may be of various shapes, sizes, or configurations. One preferred embodiment of the condenser 7 is a coiled copper tube surrounded by or embedded in graphite foam in the shape of a hollow cylinder. As the heat is removed from the condenser 7, the vapor then condenses to a liquid and is forced out of the outlet 17 of the condenser through the second nonporous connection means, which may be a return line which feeds the return tubes in the evaporator 3. Hence the cycle is completed and a totally passive cooling system is demonstrated.

Figure 5:
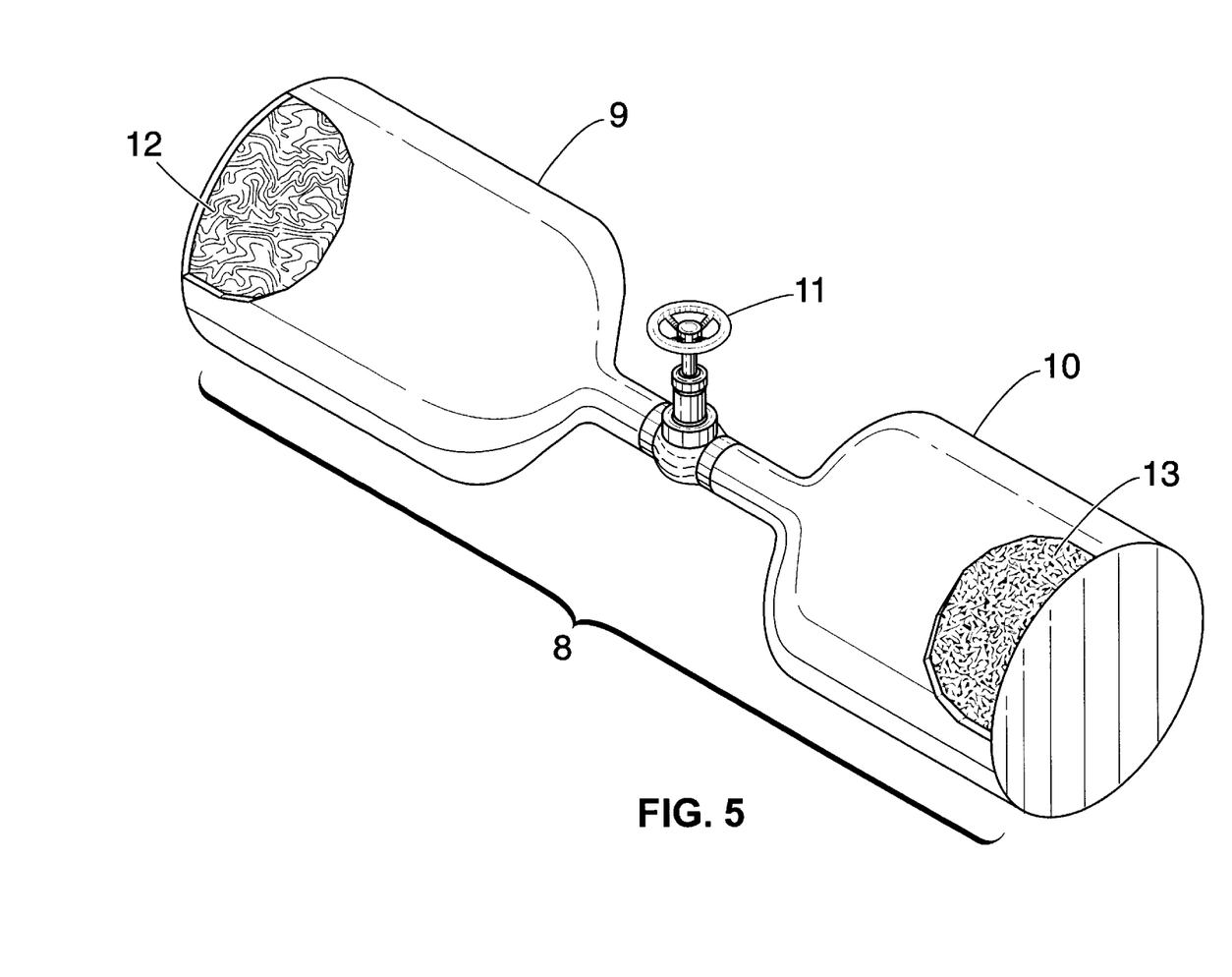
FIG. 5 shows details of the thermal battery.

One method for providing a portable cooling source is a "thermal battery" 8. The battery 8 is comprised of two chambers 9, 10 connected by a throttle valve 11. In the "hot" or adsorption side, the chamber 9 is filled with an adsorptive media 12 such as a zeolite or activated carbon. The "cold" chamber 10 is filled with graphite foam 13. The system is evacuated to a hard vacuum, $<1\times10^{-3}$ torr, and then the cold chamber 10 is filled with the appropriate amount of thermal batttery evaporating fluid 14. In a preferred embodiment, the fluid 14 is water as it has the highest latent heat of vaporization. The filling is done in a way to place all the water in the side with the foam 13 and none in the side with the activated carbon 12 with the throttle valve 11 closed.

Figure 4:
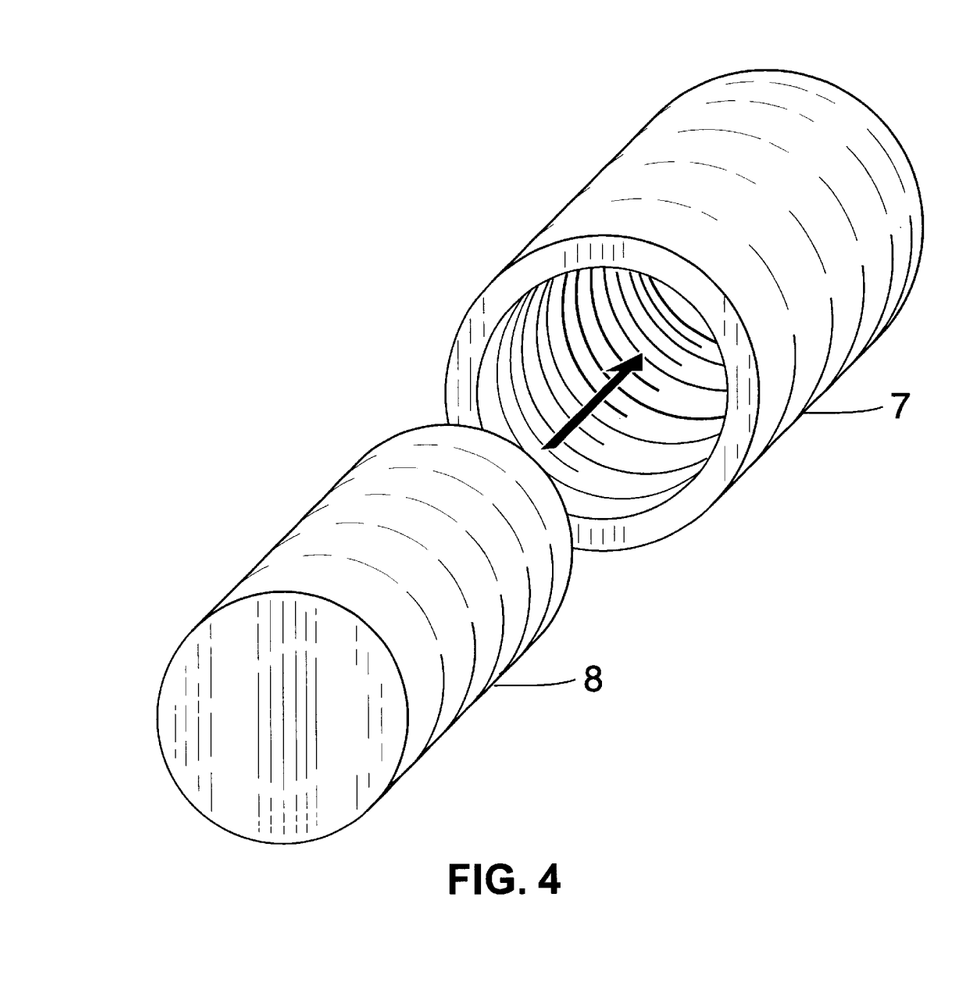
FIG. 4 shows how a thermal battery may fit with a condenser.

In use, as the throttle valve 11 is opened, water will be vaporized from the "cold" chamber 10 and traverse to the "hot" chamber 9. Since the "hot" chamber 9 is filled with an adsorbent material, the water vapor condenses, thereby continuing to drive the evaporation of the water from the "cold" chamber 10. This evaporation from the "cold" chamber 10 reduces the "cold" side temperature and therefore provides a cold chamber 10 which can be placed in the hollow condenser 7 of the cooling apparatus. The temperature of the "cold" chamber 10 of the of the thermal battery 8 can be regulated by regulating the position of the throttle valve 11, and hence an inherent thermostat and computer control may easily be fitted. This would also regulate the temperature of the cooling apparatus.

The cooling apparatus described herein may be utilized to cool the body of a living wearer as it is worn between the wearer's body and an outer garment or shield which protects the wearer from hazards. Such outer garments or shields might include space suits, projectile-protective shields, edged weapon-protective shields, impact-protective shields, explosion-protective shields, heat-protective shields, poison-protective suits or shields, microbe-protective suits or shields, corrosive agent-protective suits or shields, radiation-protective suits or shields, and the like. In some embodiments, such suits or shields, the structures of which are known to the skilled artisan, may comprise layers of the apparatus.

While there has been shown and described what are at present considered the preferred embodiments of the invention, it will be obvious to those skilled in the art that various changes and modifications can be made therein without departing from the scope of the inventions defined by the appended claims.

What is claimed is:

1. A thermal-battery augmented, closed-cycle apparatus for cooling a living body comprising:
    A A heat pickup body configured to cover at least a portion of a living body and comprising:
    I A flexible, impermeable contact foil configured to be in proximate contact with the living body;
    II A liquid-permeable evaporator layer disposed in surface contact with said contact foil;
    III Porous liquid conduit means disposed within and throughout said liquid permeable evaporator layer for conducting a liquid therethrough and further comprising a first non-porous connection means for communicably connecting said porous liquid conduit means;
    IV A semi-rigid, gas-permeable gas conduit layer disposed in surface contact with said liquid permeable evaporator layer and further comprising a second non-porous connection means for communicably connecting said semi-rigid gas-permeable gas conduit layer; and,
    V A flexible, impermeable cover foil disposed in surface contact with said semi-rigid gas-permeable layer;
    VI Said flexible, impermeable contact foil, said liquid-permeable evaporator layer, said semi-rigid gas-permeable conduit layer, and said flexible, impermeable cover foil being sealed on all edges to prevent communication between each layer and atmosphere;
    B A condenser comprising a chamber and being suitably configured so that said condenser may be disposed in thermal contact with a thermal battery for transferring heat from said condenser to the thermal battery, said chamber communicably connected to said first connection means and said second connection means so that said heat pickup body, first connection means, second connection means, and condenser form a continuous sealed system;
    C A heat pickup body evaporating fluid contained within the sealed system; and
    D A thermal battery configured to be disposed in thermal contact with said condenser, said thermal battery further comprising:
        I An adsorption chamber, said adsorption chamber at least partially filled with an adsorptive media;
        II An evaporation chamber, said evaporation chamber suitably configured so that the evaporation chamber may be placed in thermal contact with the condenser;
        III A closable throttle valve, said throttle valve being communicably connected between said absorption chamber and said evaporation chamber; said adsorption chamber, evaporation chamber, and throttle valve configured to form a sealed thermal battery system; and,
        IV A thermal battery evaporating fluid, said thermal battery evaporating fluid contained within the sealed thermal battery system.

2. A thermal-battery augmented, closed-cycle body armor protective apparatus for protecting and cooling a living body comprising:
    A A heat pickup body configured to cover at least a portion of a living body and comprising:
    I A flexible, impermeable contact foil configured to be in proximate contact with the living body;
    II A liquid-permeable evaporator layer disposed in surface contact with said contact foil;
    III Porous liquid conduit means disposed within and throughout said liquid permeable evaporator layer for conducting a liquid therethrough and further comprising a first non-porous connection means for communicably connecting said porous liquid conduit means;
    IV A semi-rigid, gas-permeable gas conduit layer disposed in surface contact with said liquid permeable evaporator layer and further comprising a second non-porous connection means for communicably connecting said semi-rigid gas-permeable gas conduit layer; and,
    V A flexible, impermeable cover foil disposed in surface contact with said semi-rigid gas-permeable layer;
    VI Said flexible, impermeable contact foil, said liquid-permeable evaporator layer, said semi-rigid gas-permeable conduit layer, and said flexible, impermeable cover foil being sealed on all edges to prevent communication between each layer and atmosphere;

B  A condenser, said condenser further comprising a chamber and being suitably configured so that said condenser may be disposed in thermal contact with a thermal battery for transferring heat from said condenser to the thermal battery, said chamber communicably connected to said first connection means and said second connection means so that said heat pickup body, first connection means, second connection means, and condenser form a continuous, sealed system;

C  A heat pickup body evaporating fluid contained within the sealed system; and, D  A thermal battery, said thermal battery further comprising:
   I  An adsorption chamber, said adsorption chamber at least partially filled with an adsorptive media;
   II  An evaporation chamber, said evaporation chamber suitably configured so that the evaporation chamber may be placed in thermal contact with the condenser;
   III  A closable throttle valve, said throttle valve being communicably connected between said absorption chamber and said evaporation chamber, said adsorption chamber, evaporation chamber, and throttle valve configured to form a sealed thermal battery system;
   IV  A thermal battery evaporating fluid, said thermal battery evaporating fluid contained within the sealed thermal battery system; and, E  a protective shield disposed proximate to and covering at least a portion of said heat pick-up body, for protecting the living body.

3. The apparatus according to claim 1 or 2, wherein said adsorptive media in said adsorption chamber comprises a material selected from the group consisting of zeolite and activated carbon.

4. The apparatus according to claim 1 or 2 in which said evaporation chamber is at least partially filled with graphite foam.

5. The apparatus according to claim 1 or 2 in which the flow rate through said closable throttle valve may be varied by a user.

6. The apparatus according to claim 1 or 2 in which said thermal battery evaporating fluid comprises water.

* * * * *